United States Patent [19]

Umezawa et al.

[11] Patent Number: 5,288,898
[45] Date of Patent: Feb. 22, 1994

[54] N-METHYLPHENYLSERINE ALKYL ESTER DERIVATIVES AND USES THEREOF

[75] Inventors: Hamao Umezawa, Tokyo; Toshiharu Nagatsu, Nagoya; Tomio Takeuchi, Tokyo; Hajime Morishima, Tokyo; Yoshio Sawasaki, Tokyo; Hiroshi Takezawa, Tokyo; Fujinori Sasaki, Okazaki, all of Japan

[73] Assignee: Zaidan Hojim Biseibutsu Kagaku Kenkyu Kai, Japan

[21] Appl. No.: 56,619

[22] Filed: May 4, 1993

Related U.S. Application Data

[63] Continuation of Ser. No. 887,248, May 19, 1992, abandoned, which is a continuation of Ser. No. 765,420, Sep. 25, 1991, abandoned, which is a continuation of Ser. No. 605,154, Oct. 31, 1990, abandoned, which is a continuation of Ser. No. 394,146, Aug. 16, 1989, abandoned, which is a continuation of Ser. No. 258,124, Oct. 13, 1988, abandoned, which is a continuation of Ser. No. 913,764, Sep. 30, 1986, abandoned.

[30] Foreign Application Priority Data

Sep. 30, 1985 [JP] Japan .................................. 214993

[51] Int. Cl.$^5$ ................... C07C 229/36; A61K 31/24
[52] U.S. Cl. ........................ 560/40; 562/446
[58] Field of Search .................. 560/40; 562/446; 514/538, 567

[56] References Cited

FOREIGN PATENT DOCUMENTS 54-138537 10/1979 Japan .................................. 574/538
59-216858 5/1983 Japan .
60-132935 7/1985 Japan .................................. 560/40

OTHER PUBLICATIONS

Microbiological Research Foundation I, *Chemical Abstracts*, vol. 101, No. 198196p (1984).
Microbiological Research Foundation II, *Chemical Abstracts*, vol. 100, No. 175293h (1984).
Chemical Abstracts 94: 4247z (1980).
Castellucci et al., *Arzneim.-Forsch*, 29(1), pp. 27-31 (1979).
Microbial Research Foundation I, *Chemical Abstracts*, vol. 101, No. 198196p (1984).
Microbial Research Foundation II, *Chemical Abstracts*, vol. 100, No. 175293h (1984).

*Primary Examiner*—Paul J. Killos
*Assistant Examiner*—B. Frazier
*Attorney, Agent, or Firm*—Larson and Taylor

[57] ABSTRACT

As new compounds are now provided N-methyl-3-(3,4-dihydroxyphenyl)serine alkyl esters which are effective as an α-adrenergic and β-adrenergic agent to stimulate the α-adrenergic and β-adrenergic functions of the central nervous system of mammalian animals and are expectable to be useful for therapeutic treatment of disorders as invoked by reduced biological activities or functions of the α- and/or β-adrenergic neurons. N-methyl-L-threo-3-(3,4-dihydroxyphenyl)serine ($C_1$-$C_6$) alkyl esters are preferred amongst the new compounds of this invention.

5 Claims, No Drawings

N-METHYLPHENYLSERINE ALKYL ESTER DERIVATIVES AND USES THEREOF

This application is a continuation of application Ser. No. 07/887,248 filed May 19, 1992, now abandoned, which is a continuation of application Ser. No. 07/765,420 filed Sep. 25, 1991, now abandoned which is a continuation of Ser. No. 07/605,154, filed Oct. 31, 1990, now abandoned, which is a continuation of Ser. No. 07/394,146, filed Aug. 16, 1989, now abandoned, which is a continuation of Ser. No. 07/258,124, filed Oct. 13, 1988, now abandoned, which is a continuation of Ser. No. 06/913,764, filed Sep. 30, 1986, now abandoned.

SUMMARY OF THE INVENTION

This invention relates to N-methyl-3-(3,4-dihydroxyphenyl)serine alkyl esters which are new compounds having enhanced activities of antagonising the pharmacological effects of reserpine and of reducing the hypothermia and ptosis as induced by administration of reserpine in mammalian animals and which are active as a central nervous system stimulant and are expectable to be useful in the therapeutic treatment of disorders of the central nervous system of mammalian animals, including man, such as mental depressions, Parkinsonism and Senile dementia. This invention also relates to a pharmaceutical composition comprising the above-mentioned new compound as active ingredient. This invention further relates to a process for the production of the above-mentioned new compounds.

BACKGROUND OF THE INVENTION

We, the present inventors, already synthetized and provided N-methyl-D,L-threo-3-(3,4-dihydroxyphenyl)serine and N-methyl-L-threo-3-(3,4-dihydroxyphenyl)serine, and N-methyl-L-threo-3-(3,4-dihydroxyphenyl)serine may also be termed as L-threo-adrenalinecarboxylic acid and is a compound which is able to penetrate into the brain of mammalian animals when administered intravenously and to increase the levels of the physiologically active mono-amines in vivo and especially the level of adrenaline in the brain and hence exhibits different pharmacological effects (Japanese patent application first application "Kokai" Nos. 225044/83 and 112914/84; E.P. patent application publication No. 0112606; U.S. patent application Ser. No. 523,957 and U.S. patent application Ser. No. 768,345).

The L-threo-adrenalinecarboxylic acid is now studied for its pharmacological activities and expected to be useful as antidepressant and as anti-Parkinsonism drug.

On the other hand, L-threo-3-(3,4-dihydroxyphenyl)serine which is sometimes termed as L-threo-DOPS is known to have some activities on the circulatory system and psychotropic activities and also is expected to be useful as anti-Parkinsonism agent like to the known L-Dopa (Japanese patent application first publication "Kokai" Nos. 49252/75; 32540/76; 36233/79 and EP patent application publication No. 0024210).

In the recent years, we have continued our extensive research on the N-methyl-3-(3,4-dihydroxyphenyl)serine to find out that this compound exhibits various and useful physiological activities, and that N-methyl-L-threo-3-(3,4-dihydroxyphenyl)serine, namely the L-threo-adrenalinecarboxylic acid is able to penetrate into the brain of mammalian animals through the blood-brain barrier when administered intravenously or intraperitoneally and is able to increase the level of adrenaline in the brain through unknown biological mechanisms. As long as we are aware of, however, synthetic derivatives of the N-methyl-3-(3,4-dihydroxyphenyl)serine have not yet been produced and have not been disclosed in any literatures.

In an attempt to provide new compounds which can exhibit better pharmacological properties than the L-threo-adrenalinecarboxylic acid, we have studied on the synthetic production of new derivatives of N-methyl-3-(3,4-dihydroxyphenyl)serine. As a result, we have now found that such lower alkyl esters of the N-methyl-3-(3,4-dihydroxyphenyl)serine as represented by the general formula (I) shown below can be produced as the new compounds and are capable of exhibiting excellent pharmacological activities. In particular, we have found that N-methyl-L-threo-3-(3,4-dihydroxyphenyl)serine lower alkyl esters are able to exhibit higher activities of antagonising the psychopharmacological effects of reserpine in mammalian animals and of reducing the hypothermia and ptosis as induced by the administration of reserpine, and that the new compounds, N-methyl-3-(3,4-dihydroxyphenyl)serine lower alkyl esters (the carboxylates) and particularly N-methyl-L-threo-3-(3,4-dihydroxyphenyl)serine lower alkyl esters (the carboxylates) are active as a central nervous system stimulant and are expectable to be effective in therapeutic treatment of some disorders of the central nervous system of man, such as mental depressions, Parkinsonism and senile dementia. According to M. Bourin et al (the "Arzneim-Forsh." Vol. 33, (II), No. 8, 1173–1176 (1983)), the psychopharmacological study of the effects of various known 21 antidepressive or anti-Parkinsonism agents on the reserpine-induced hypothermia, ptosis and akinesia (reduction of motor activity) has revealed that such drugs stimulating the $\beta$-adrenergic receptors of the central nervous system directly or indirectly are active to antagonise the reserpine-induced hypothermia, that such drugs stimulating the $\alpha$-adrenergic or serotonergic receptors are active to antagonise the reserpine-induced ptosis (eyelid closing), and that such drugs stimulating the dopaminergic receptors are active to antagonise the reserpine-induced akinesia. Accordingly, we have now considered it evident from our tests that at least, the new compounds, N-methyl-L-threo-3-(3,4-dihydroxyphenyl)serine lower alkyl esters according to this invention are active to stimulate both the $\alpha$- and $\beta$-adrenergic functions of the central nervous system of mammalian animals. This is in contrast to that neither of the N-methyl-L-threo-3-(3,4-dihydroxyphenyl)serine (namely, the free L-threo-adrenalinecarboxylic acid) and L-threo-DOPS do actually antagonise the effect of reserpine to induce the ptosis and hence are evidently not active to stimulate the $\alpha$-adrenergic functions, as demonstrated in our tests shown hereinafter.

DETAILED DESCRIPTION OF THE INVENTION

According to a first aspect of this invention, therefore, there is provided an N-methyl-3-(3,4-dihydroxyphenyl)serine alkyl ester of the formula (I)

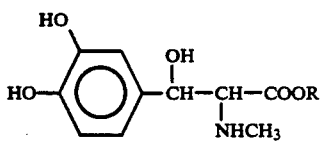

(I)

wherein R denotes a lower alkyl group, or a pharmaceutically acceptable salt thereof.

The compound of the formula (I) above contains two asymmetric carbon atoms in the molecule thereof and so there exist four steric isomers, namely the D-threo-isomer, L-threo-isomer, D-erythro-isomer and L-erythro-isomer. The new compound of the formula (I) according to this invention encompasses all the possible steric isomers thereof.

According to a preferred embodiment of the first aspect of this invention, there is provided an N-methyl-L-threo-3-(3,4-dihydroxyphenyl)serine lower-alkyl ester or a pharmaceutically acceptable acid-addition salt thereof.

In accordance with this invention, the term "lower alkyl" group includes linear or branched alkyl groups containing 1 to 6 carbon atoms, such as methyl group, ethyl group, n-propyl group, isopropyl group, n-butyl group, isobutyl group, tert-butyl group, n-pentyl group, iso-pentyl group, n-hexyl group and the like.

The pharmaceutically acceptable salt of the compound of the formula (I) according to this invention includes salts of the compound (I) with a pharmaceutically acceptable inorganic acid such as hydrochloric acid, hydrobromic acid, sulfuric acid, nitric acid, phosphoric acid and the like, or with a pharmaceutically acceptable organic acid such as acetic acid, trifluoroacetic acid, oxalic acid, malic acid, maleic acid, fumaric acid, citric acid, tartaric acid, methanesulfonic acid, p-toluenesulfonic acid and the like.

Representative examples of the compound of the formula (I) according to this invention are listed below:

(1) N-methyl-D,L-threo-3-(3,4-dihydroxyphenyl)serine methyl ester
(2) N-methyl-D-threo-3-(3,4-dihydroxyphenyl)serine methyl ester
(3) N-methyl-L-threo-3-(3,4-dihydroxyphenyl)serine methyl ester
(4) N-methyl-D,L-erythro-3-(3,4-dihydroxyphenyl)serine methyl ester
(5) N-methyl-D-erythro-3-(3,4-dihydroxyphenyl)serine methyl ester
(6) N-methyl-L-erythro-3-(3,4-dihydroxyphenyl)serine methyl ester
(7) N-methyl-D,L-threo-3-(3,4-dihydroxyphenyl)serine ethyl ester
(8) N-methyl-D-threo-3-(3,4-dihydroxyphenyl)serine ethyl ester
(9) N-methyl-L-threo-3-(3,4-dihydroxyphenyl)serine ethyl ester
(10) N-methyl-D,L-erythro-3-(3,4-dihydroxyphenyl)serine ethyl ester
(11) N-methyl-D-erythro-3-(3,4-dihydroxyphenyl)serine ethyl ester
(12) N-methyl-L-erythro-3-(3,4-dihydroxyphenyl)serine ethyl ester
(13) N-methyl-D,L-threo-3-(3,4-dihydroxyphenyl)serine n-propyl ester
(14) N-methyl-L-threo-3-(3,4-dihydroxyphenyl)serine n-propyl ester
(15) N-methyl-L-threo-3-(3,4-dihydroxyphenyl)serine isopropyl ester
(16) N-methyl-L-threo-3-(3,4-dihydroxyphenyl)serine n-butyl ester
(17) N-methyl-L-threo-3-(3,4-dihydroxyphenyl)serine isobutyl ester
(18) N-methyl-L-threo-3-(3,4-dihydroxyphenyl)serine tert-butyl ester
(19) N-methyl-L-threo-3-(3,4-dihydroxyphenyl)serine n-pentyl ester
(20) N-methyl-L-threo-3-(3,4-dihydroxyphenyl)serine isopentyl ester
(21) N-methyl-L-threo-3-(3,4-dihydroxyphenyl)serine n-hexyl ester According to a second aspect of this invention, there is provided a pharmaceutical composition comprising an effective amount of an N-methyl-3-(3,4-dihydroxyphenyl) serine alkyl ester of the formula (I) or a pharmaceutically acceptable acid addition salt thereof as the active ingredient, in association with a pharmaceutically acceptable carrier for the active ingredient. This pharmaceutical composition of this invention may be for use in preventive or therapeutic treatment of some disorders of the central nervous system in mammalian animals, including man, and this composition may be used especially for stimulation of the α- and β-adrenergic functions of the central nervous system of a mammalian animal, including man.

According to a third aspect of this invention, there is provided an α-adrenergic and β-adrenergic agent comprising an N-methyl-L-threo-3-(3,4-dihydroxyphenyl)serine ($C_1$–$C_6$)alkyl ester or a pharmaceutically acceptable acid addition salt thereof.

According to a fourth aspect of this invention, there is provided a method of stimulating the α- and β-adrenergic functions of the central nervous system of a patient who is suffering from a disorder as invoked by reduced biological effects of the α- and/or the β-adrenergic neurons, which comprises administering orally, intravenously, intraperitonearlly or rectally to the patient an effective amount of an N-methyl-L-threo- 3-(3,4-dihydroxyphenyl)serine ($C_1$–$C_6$)alkyl ester or a pharmaceutically acceptable acid addition salt thereof.

The pharmaceutical composition of this invention may be formulated into various, conventional forms by mixing with one or more pharmaceutically acceptable carriers, excipients and/or other addtivies, so that the formulations so made are suitable for oral or non-oral administration. Examples of such carriers may be organic and inorganic inert carrier materials suitable for the oral and parenteral administrations, such as water and ethanol. The available additives include a binder such as gum arabic, gelatine, tragacanth gum, CMC-Na; an excipient such as lactose and starch; a lubricant such as magnesium stearate, talc and polyethylene glycol; a disintegrating agent such as starch and CMC-Ca; and a base such as a vegetable oils, yellow soft vaseline and lanoline. The pharmaceutical compositions may be in the form of solid formulations such as tablet, powder, fine granules, capsule, pill and suppository, or in the form of liquid formulations such as solution, emulsion, injectable solution or suspension, or in the form of semisolid formulations such as ointment. The pharmaceutical compositions may be in sterile state and may contain one or more conventional adjuvants such as preservatives, stabilizers, wetting agents, emulsifying agents, isotonizing salts, buffering agents and the like, as the occasion demands. If desired, the pharmaceutical compositions may further contain any additional, medicinal substances. The pharmaceutical compositions of this invention may preferably be formulated so that one dosage unit contains about 10 mg to about 500 mg of the active compound of the formula (I) of this invention. The pharmaceutical compositions of this invention may contain an amount of, for example, 10% to 90% by weight of the N-methyl-3-(3,4-dihydroxyphenyl) serine alkyl ester of the formula (I) or a pharmaceutically acceptable acid addition salt thereof.

The dose of the compound of the formula (I) according to this invention to be given to the patient may be varied depending on the symptons of the disorder, age of the patient, body weight, and other various factors, and only for a guideline, a usual dosage of the compound of the formula (I) is in a range of about 1 mg to about 20 mg/kg for adult once daily upon the oral administration and in a range of about 0.1 mg to 5 mg/kg for adult once daily upon the parenteral administration.

The process for the production of the compound of the formula (I) according to this invention is now described. Principally, the compound of the formula (I) may be produced by esterifying N-methyl-3-(3,4-dihydroxyphenyl)serine with a lower alkanol in a known manner for the esterification of a free carboxylic acid with alcohol.

According to a fifth aspect of this invention, therefore, there is provided a process of producing an N-methyl-3-(3,4-dihydroxyphenyl)serine alkyl ester of the formula (I)

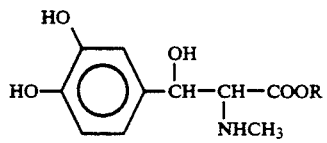

wherein R is a lower alkyl group, which comprises reacting an unprotected or N,O-protected N-methyl-3-(3,4-dihydroxyphenyl)serine of the formula (II)

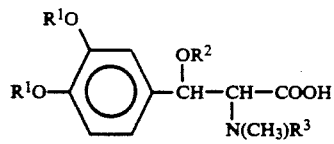

wherein $R^1$ and $R^2$ are each a hydrogen atom or a hydroxy-protecting group and $R^3$ is a hydrogen atom or an amino-protecting group, or a reactive derivative of the compound (I), with an alkanol of the formula (III)

R—OH  (III)

wherein R is the lower alkyl group, or a reactive derivative of said alkanol, in an organic solvent, and then removing the residual hydroxyl-protecting groups and amino-protecting group from the resulting reaction product compound where these protective groups are remaining in the reaction product compound.

It is to be noticed that when the final compound of the formula (I) is to be in the from of the L-threo-isomer, the starting serine compound of the formula (II) should preferably be in the form of the L-threo-isomer, and that when the final compound of the formula (I) is to be in the form of the D,L-threo-isomer, the starting serine compound of the formula (II) is similarly in the form of the DL-threo-isomer. When the final compound (I) in the form of the L-threo-isomer is to be obtaind even with starting from the DL-threo-form of the starting serine compound (II), it is necessary to separate the racemic mixture of the resulting esterification product compounds into the D-isomer and the L-isomer by an appropriate steric dissolution method.

The esterification reaction as involved in the present process may be performed in any manner known in the conventional technique of esterifying carboxylic acid with alcohol. To achieve an efficient and commercial production of the compound of the formula (I), however, it is preferable to carry out the present process according to any of the following procedures (1), (2) and (3):

(1) According to the first procedure, an unprotected or N,O-protected N-methyl-3-(3,4-dihydroxyphenyl) serine of the formula (II) is condensed with an alkanol of the formula (III) with the dehydration reaction. This dehydrative condensation may be effected, for example, according to methods (a), (b), (c) or (d) as described below:

(i) Method (a): The dehydrative condensation is effected by heating a solution or suspension of the starting serine compound (II) in an alkanol (III) at a temperature of up to the refluxing temperature of the alkanol as employed, in the presence of an acidic catalyst such as hydrogen chloride, p-toluenesulfonic acid, sulfuric acid and the like.

(ii) Method (b): The dehydrative condensation is effected by heating a solution or suspension of the starting serine compound (II) in an alkanol (III) in the presence of a dehydrating agent such as dicyclohexylcarbodiimide (DCC) and in the absence or presence of a catalyst, preferably a basic catalyst such as pyridine, 4-dimethylaminopyridine, a tri-alkylamine, especially tri-ethylamine, and the like.

(iii) Method (c): The dehydrative condensation is effected by heating a solution or suspension of the starting serine compound (II) and an alkanol (III) in an aprotic, polar organic solvent, preferably dimethylformamide (DMF) and in the present of oxalic acid chloride so that there is formed dimethylforminium chloride (Vilsmeier reagent) which promotes the condensation and also serves as the reaction medium.

(iv) Method (d): The dehydrative condensation is effected by heating a solution or suspension of the starting serine compound (II) in an alkanol (III) in the presence of a rodex system comprising triphenylphosphine or triethyl phosphite and an azodicarboxylic acid alkyl ester.

(2) According to the second procedure, an unprotected or N,O-protected N-methyl-3-(3,4-dihydroxyphenyl) serine alkali metal salt (carboxylate) as a reactive derivative (the reactive equivalent) of the starting serine compound of the formula (II) is reacted with an alkyl halide or sulfonate of the formula (IV)

R—X  (IV)

wherein R is the lower alkyl group and X is a halogen atom or an organic sulfonyloxy group, preferably methanesulfonyloxy and toluenesulfonyloxy group, as a reactive derivative of the alkanol reagent of the formula (III), with liberation of the metal halide or sulfonate (the salt). This condensation reaction with liberation of the salt may be carried out in an anhydrous, organic solvent such as acetone, ethyl ether, acetonitrile, dimethylformamide and the like or in mixed organic solvents of two or more of said particular solvents and in the absence or presence of a known acid-binder such as an alkali metal hydride, an alkali metal or alkaline earth metal carbonate and a tri-alkylamine, especially tri-ethylamine.

(3) According to the third procedure, an acid anhydride, active ester or mixed acid anhydrides as derived from an unprotested or N,O-protected N-methyl-3-(3,4-dihydroxyphenyl)serine is employed as an activated derivative (the reactive equivalent) at the carboxylic radical of the starting serine compound of the formula (II), and the former activated serine derivative is reacted with an alkanol of the formula (III) in an inert, organic solvent such as tetrahydrofuran, chloroform, acetonitrile and the like, and in the presence of a basic compound such as pyridine and tri-ethylamine which may also serve as a dehydrohalogenating agent.

The acid halide (as an activated equivalent derivative) of the serine compound of the formula (II) which is employed as a starting material in the present process of this invention may be prepared by chlorinating the serine compound (II) (the free carboxylic acid form) with thionyl halide, preferably thionyl chloride. The active ester (as an activated reactive derivative) of the serine compound (II) may be prepared by reacting the serine compound (II) (the free carboxylic acid form) with e.g. 1-hydroxytriazole (HOBT) in the presence of a condensation agent such as DCC. The mixed acid anhydrides (as a reactive equivalent derivative) of the serine compound (II) may be prepared by reacting the serine compound (II) (the free carboxylic acid form) with ethyl chloroformate in the presence of a basic compound such as sodium carbonate.

The process of the fifth aspect of this invention may be performed not only according to the above-mentioned procedures (1) to (3) but also according to other known procedures of esterification of carboxylic acids. For instance, the present process may also be accomplished according to a method of Mukaiyama et al using $\alpha$-halopyridinium salt (see the "Chem. Lett." 13 (1976)), or according to a known alkylation method using a diazoalkane such as diazomethane.

For the production of N-methyl-3-(3,4-dihydroxyphenyl) serine methyl ester, there is available a further process in which an O-protected 3-(3,4-dihydroxyphenyl)serine such as DL- or L-threo-3-(3,4-dibenzyloxyphenyl)serine is reacted with dimethyl sulfate in an inert organic acid such as acetone in such a manner that the N-methylation and the esterification of the carboxylic group of the serine moiety take place concurrently to give the corresponding O-protected N-methyl-3-(3,4-dihydroxyphenyl)serine methyl ester, such as N-methyl-DL- or L-threo-3-(3,4-dibenzyloxyphenyl)serine methyl ester which is subsequently subjected to a known deprotection step for the removal of the remaining hydroxyl-protecting benzyl groups, affording the aimed N-methyl-3-(3,4-dihydroxyphenyl)serine methyl ester (see Example 6 given hereinafter).

In the present process, an N,O-protected derivative of the serine compound (II) may be used as starting material. In the N,O-protected N-methyl-3-(3,4-dihydroxyphenyl)serine of the formula (II), the hydroxyl-protecting group $R^1$ is to protect the "aromatic" or catecolic hydroxyl group and may be, for example, benzyl group, methoxymethyl group, tert-butoxycarbonyl group and other known catecolic hydroxyl-protecting group. The hydroxyl-protecting group $R^2$ is to protect the "aliphatic" hydroxyl group and may be, for example, benzyl group, tetrahydropyranyl group and the like. The amino-protecting group $R^3$ may be any known amino-protecting group conventionally used in the synthesis of peptides and may be, for example, an aralkyl group such as benzyl, an aralkyloxycarbonyl group such as benzyloxycarbonyl, and an alkoxycarbonyl group such as tert-butoxycarbonyl.

When the reaction product compound as formed by the reaction of the serine compound (II) with an alkanol (III) is still containing the residual hydroxy-protecting groups ($R^1$, $R^2$) and/or the residual amino-protecting group ($R^3$), these remaining protective groups are removed by appropriate methods for the deprotection, depending on the nature of the residual O-protecting groups and N-protecting groups. For instance, the benzyl group and benzyloxycarbonyl group may be cleaved by catalytic hydrogenolysis in a known manner. The methoxymethyl group, tetrahydropyranyl group and tert-butoxycarbonyl group may be cleaved in a known manner by acid hydrolysis with trifluoroacetic acid and the like.

The final serine compound of the formula (I) so produced may be isolated and purified according to conventional techniques such as concentration, extraction, column chromatography, recrystallization and other methods.

To demonstrate the useful pharmacological activities of the new compounds of the formula (I) according to this invention, the particular four substances as listed below were selected as typical examples of the new compounds of this invention.

| Test Compound Abbreviation | Nomination |
| --- | --- |
| Compound A | N-methyl-L-threo-3-(3,4-dihydroxyphenyl)serine methyl ester oxalate |
| Compound B | N-methyl-L-threo-3-(3,4-dihydroxyphenyl)serine ethyl ester oxalate |
| Compound C | N-methyl-L-threo-3-(3,4-dihydroxyphenyl)serine n-propyl ester oxalate |
| Compound D | N-methyl-L-threo-3-(3,4-dihydroxyphenyl)serine n-butyl ester oxalate |

As the pharmacological effect of medicinal substance acting on the central nervous system of mammalian animals, including man, are normally estimated in the term of their effects of antagonising the psychopharmacological effects of reserpine, a known anti-psychopharmacological agent, we conducted some tests of evaluating the effects of the above-mentioned four particular substances according to this invention to antagonise the psychopharmacological effects of reserpine which would induce a decrease in the body temperature (the hypotermia) and also induce closing of the eyelid (the ptosis) in mammalian animals, such as mice (see the aforesaid "Arzneim-Forsch." Vol. 33 (II), No. 8, 1173–1176 (1983)),whereby the utilities of the new compounds of this invention are illustrated.

Pharmacological Test No. 1

To ddY-strain mice (male, body weight 20–30 g, five mice in each group or ten mice in each group) was subcutaneously administered 2.5 mg/kg of reserpine. 8 Hours after the administration of reserpine, the mice having received reserpine were estimated in respect of their eyelid closing (the ptosis) and the decrease in their body temperature (the hypothermia) as induced by reserpine. Just after this estimation, the mice were further administered intraperitoneally or orally with the test compound as identified in the Tables below. After the administration of the test compound, the eyelid closing (the ptosis) and the body temperature of the mice were evaluated at one-hour-intervals during the lapse of 3 hours. In this way, the effects of the test compound to antagonise the ptosis and hypothermia induced by reserpine were examined and recorded.

The score system for the eyelid closing (the ptosis) was according to a modification of the score system of Rubin et al (the "Journal of Pharmacological Experimental Therapy" Vol. 120,125 (1957)) and was scaled on the following basis. Thus, the degree of the eyelid closing was scored depending on the extent of the upper eyelid to fall down from the normal state of the upper eyelid of the intact mice which were not treated with any drug.

The determination of the body temperature was made with an electric, thermometer MGA-III-219 (a product commercially available from Nihon Koden Company Ltd., Japan) which was inserted rectally into the mouse.

The number of the test animals was 10 for the Control mice group (Reference group having received the administration of reserpine but not the administration of the test compound), while the number of the test animals was 5 for the Treated mice group (the mice group having received the administration of reserpine as well as the administration of the test compound) in respect of each test compound.

For the comparison purpose, L-threo-3-(3,4-dihydroxyphenyl)serine (L-threo-DOPS) and N-methyl-L-threo-3-(3,4-dihydroxyphenyl)serine (L-threo-adrenaline-carboxylic acid; abbreviated as L-threo-ADCA) were tested in the same manner as above.

The test results obtained (as the average) are summarised in Tables 1 and 2 below.

TABLE 1

| | | | | | | | |
|---|---|---|---|---|---|---|---|
| | | Effects of test compound on the reserpine-induced hypothermia | | | | | |
| | Number | Administration | | Body temperature (°C.) at the end of 8 hours | Body temperature (°C.) at the end of 1, 2 or 3 hours after administration of test compound | | |
| Test Compound | of mice tested | Dosage (mg/kg) | Route | after administration of reserpine | 1 Hour | 2 Hour | 3 Hours |
| Reference group (untreated with test compound) | 10 | — | — | 28.8 ± 0.9 | 28.2 ± 0.8 | 27.6 ± 1.0 | 27.7 ± 1.0 |
| Compound A | 5 | 1000 | Oral | 29.1 ± 0.9 | 31.9 ± 1.2* | 33.2 ± 1.2*** | 32.7 ± 0.7*** |
| Compound B | 5 | 200 | Intraperitoneal | 27.7 ± 0.9 | 31.7 ± 0.6** | 32.0 ± 0.3* | 31.0 ± 0.4* |
| L-threo-DOPS (comparative) | 5 | 1000 | Oral | 28.2 ± 0.7 | 28.0 ± 0.6 | 30.7 ± 0.7 | 32.0 ± 0.8* |
| L-threo-ADCA (comparative) | 5 | 200 | Intraperitoneal | 28.5 ± 0.8 | 29.9 ± 0.6 | 31.3 ± 1.0* | 31.1 ± 0.4* |

Notes:
the asterisk * denotes that the test results were significant with p of 5%;
the asterisks ** denote that the test results were significant with p of 2%, and
the asterisks *** denote that the test results were significant with p of 0.5%, when the test results were assayed according to the known Student's T assay method.

TABLE 2

| | | | | | | | |
|---|---|---|---|---|---|---|---|
| | | Effects of test compound on the reserpine-induced ptosis | | | | | |
| | Number | Administration | | Scores of ptosis at the end of 8 hours | Scores of ptosis at the end of 1, 2 or 3 hours after administration of test compound | | |
| Test Compound | of mice tested | Dosage (mg/kg) | Route | after administration of reserpine | 1 Hour | 2 Hours | 3 Hours |
| Reference group (untreated with test compound) | 10 | — | — | 3.0 ± 0.0 | 3.0 ± 0.0 | 3.0 ± 0.0 | 3.0 ± 0.0 |
| Compound A | 5 | 1000 | Oral | 3.0 ± 0.0 | 0 ± 0.0* | 0.0 ± 0.0* | 0.8 ± 0.4 |
| Compound B | 5 | 200 | Intraperitoneal | 3.0 ± 0.0 | 1.4 ± 0.4* | 2.0 ± 0.5 | 2.2 ± 0.4 |
| L-threo-DOPS (comparative) | 5 | 1000 | Oral | 3.0 ± 0.0 | 3.0 ± 0.0 | 3.0 ± 0.0 | 3.0 ± 0.0 |
| L-threo-ADCA (comparative) | 5 | 200 | Intraperitoneal | 3.0 ± 0.0 | 3.0 ± 0.0 | 3.0 ± 0.0 | 3.0 ± 0.0 |

Notes:
the asterisk * denotes that the test results were significant with an error probability of 1% when assayed by the U assay method.

| Ptosis scores | Degree of Eyelid Closing |
|---|---|
| 0 | Eyelids completely opened as observed with intact mice |
| 1 | Eyelids more than ½ opened |
| 2 | Eyelids ½ or less opened |
| 3 | Eyelids completely closed. |

Pharmacological Test No. 2

The test procedure of Pharmacological Test No. 1 above for estimation of the reserpine-induced hypothermia antagonism was repeated with Compounds C and D of this invention as identified hereinbefore.

The test results obtained (as the average) are summarized in Table 3 below.

TABLE 3

| | | | | Body temperature (°C.) | Body temperature (°C.) at the end of 1, 2 or 3 hours after administration of test compound | | |
|---|---|---|---|---|---|---|---|
| Test Compound | Number of mice tested | Administration Dosage (mg/kg) | Route | at the end of 8 hours after administration of reserpine | 1 Hour | 2 Hour | 3 Hours |
| Reference group (untreated with test compound) | 10 | — | — | 29.2 ± 0.8 | 29.1 ± 0.1 | 28.7 ± 0.7 | 28.1 ± 0.6 |
| Compound C | 5 | 200 | Intraperitoneal | 28.0 ± 0.8 | 33.1 ± 0.8 | 32.3 ± 0.4*** | 30.8 ± 1.0* |
| Compound D | 5 | 200 | Intraperitoneal | 27.5 ± 0.8 | 30.4 ± 0.6 | 31.9 ± 1.0* | 30.3 ± 1.2 |

Notes:
the asterisk * denotes that the test results were significant with p of 5%;
the asterisks ** denote that the test results were significant with p of 2%, and
the asterisks *** denote that the test results were significant with p of 0.5%, when the test results were assayed according to the known Student's T assay method.

As will be seen from the results of Tables 1 and 2, it is evident that the Compounds A and B according to this invention are active to antagonise the effects of reserpine of decreasing the body temperature of the test animals (the hypothermia) and are also active to antagonise the effects of reserpine of inducing the eyelid falling (the ptosis), and therefore that Compounds A and B according to this invention can stimulate both the α- and β-adrenergic functions of the central nervous system. In contrast, the comparative agents, L-threo-DOPS and L-threo-ADCA can antagonise the reserpine-induced hypothermia (see Table 1) but cannot antagonise the reserpine-induced ptosis (see Table 2), and this reveals that L-threo-DOPS and L-threo-ADCA can stimulate the β-adrenergic functions but cannot stimulate the α-adrenergic functions of the central nervous system and hence both these comparative compounds are each a β-adrenergic stimulant but not any α-adrenergic stimulant, indicating that L-threo-DOPS and L-threo-ADCA can never be effective to treat therapeutically such disorders which would be invoked due to the decreased activities of or the inhibitions to the α-adrenergic functions of the central nervous system.

The production of the new compounds of this invention is now illustrated with reference to the following Examples to which this invention is not limited in any way.

EXAMPLE 1

(a) N-methyl-L-threo-3-(3,4-dibenzyloxyphenyl) serine (1.50 g) was suspended in 30 ml of methanol, and to the resulting suspension was added thionyl chloride (15 ml) under stirring and under ice-cooling. The mixture so obtained was stirred at room temperature for 30 minutes and then at 45°-50° C. for 5 hours.

The reaction solution so obtained was distilled under reduced pressure to remove the solvent, and the residue was taken up in a volume of ethyl acetate. The resultant solution was washed with aqueous 5% sodium hydroxide solution and then with water, followed by drying over anhydrous sodium sulfate. After removing the drying agent by filtration, the dried solution was distilled under reduced pressure, and the residue was dissolved into methanol, and to the methanolic solution was added 0.75 g of oxalic acid. The whole mixture was allowed to stand in an ice chamber until the crystals deposited. The crystalline product was collected by filtration, washed with a small volume of methanol and dried to afford 0.45 g of N-methyl-L-threo-3-(3,4-dibenzyloxyphenyl)serine methyl ester oxalate as colorless needles having a melting point of 127°-129° C. (with decomposition).

This final product showed the following data of the infrared absorption spectrum (IR) and the nuclear magnetic resonance absorption spectrum (NMR).

IR$\nu_{max}^{KBr}$ (cm$^{-1}$): 3500–2500, 1735, 1590, 1510, 1450, 1310, 1260, 1030, 1020, 730, 685.

NMR (CD$_3$OD/DCl) δ: 2.65 (3H,s), 3.55 (3H,s), 4.19 (1H,d. J=7.0 Hz), 5.02 (1H,d. J=7.0 Hz), 5.11 (4H,s), 6.92 (2H,s), 7.10 (1H,s), 7.26 (10H,s).

(b) The N-methyl-L-threo-3-(3,4-dibenzyloxyphenyl) serine methyl ester oxalate obtained as above (0.50 g) was dissolved in 50 ml of methanol, and to the resulting methanolic solution was added 0.1 g of 10% palladium-carbon catalyst. The hydrogenolysis was carried out at room temperature for 3 hours under a current of hydrogen gas at 1 atm. to effect the removal of the hydroxyl-protecting benzyl groups. The reaction mixture was then filtered to remove the catalyst, and the filtrate was concentrated in vacuo. The residue was triturated with ethyl ether to crystallize the deprotected product. The crystalline product so obtained was recovered by filtration, washed with ethyl ether and dried to yield 0.28 g of N-methyl-L-threo-3-(3,4-dihydroxyphenyl)serine methyl ester oxalate (Compound A as identified hereinbefore) in the form of colorless crystalline powder of a melting point of 116° to 118° C. This product showed the following IR data and NMR data.

IR$\nu_{max}^{KBr}$ (cm$^{-1}$): 3600–2400, 1740, 1600, 1530, 1450, 1410, 1295, 1125, 1055, 1000, 730.

NMR (CD$_3$OD) δ: 2.68 (3H,s), 3.56 (3H,s), 4.20 (1H,d. J=7.0 Hz), 6.50–7.00 (3H,m).

EXAMPLES 2 TO 5

The procedures of the Example 1 were repeated with replacing the methanol by ethanol, n-propanol, isopropanol or n-butanol as the corresponding alkanol. The compounds as indicated below were obtained.

Example 2

(a) N-methyl-L-threo-3-(3,4-dibenzyloxyphenyl) serine ethyl ester oxalate.
Melting point: 141°-143° C. (dec.).
IR$\nu_{max}^{KBr}$ (cm$^{-1}$): 3500–2500, 1740, 1600, 1515, 1270, 1140, 1020, 735, 725, 700.
NMR (CD$_3$OD) δ: 0.97 (3H,t. J=7.0 Hz), 2.62 (3H,s), 4.01 (2H,q. J=7.0 Hz), 4.08 (1H,d. J=8.0 Hz), 6.96 (2H,s), 7.15 (1H,s), 7.34 (10H,s).

(b) N-methyl-L-threo-3-(3,4-dihydroxyphenyl)serine ethyl ester oxalate (Compound B as identified hereinbefore).

This product showed the following IR data and NMR data.

IR$\nu_{max}^{KBr}$ (cm$^{-1}$): 3600–2400, 1735, 1600, 1460, 1405, 1290, 1050, 825, 730.

NMR (CD$_3$OD) δ: 1.05 (3H,t. J=7.0 Hz), 2.63 (3H,s), 4.01 (1H,d. J=8.0 Hz), 4.09(2H,q. J=7.0 Hz), 4.88 (1H,d. J=8.0 Hz), 6.72 (2H,s), 6.85 (1H,s).

Example 3

(a) N-methyl-L-threo-3-(3,4-dibenzyloxyphenyl) serine n-propyl ester oxalate.

Melting point: 126°–128° C. (dec.).

IR$\nu_{max}^{KBr}$ (cm$^{-1}$): 3275, 2950, 2700, 1740, 1700, 1610, 1515, 1465, 1410, 1290, 1275, 1145, 1030, 740, 725, 700.

NMR (CD$_3$OD/DCl) δ: 0.75 (3H,t. J=7.0 Hz), 1.36 (2H, sex. J=7.0 Hz), 2.62 (3H,s), 3.92 (2H,t. J=7.0 Hz), 4.11 (1H,d. J=7.0 Hz), 4.92 (1H,d. J=7.0 Hz), 5.05 (4H,s), 6.93 (2H,s), 7.11 (1H,s), 7.30 (10H,s).

(b) N-methyl-L-threo-3-(3,4-dihydroxyphenyl)serine n-propyl ester oxalate (Compound C as identified hereinbefore).

This product showed the following IR data and NMR data.

IR$\nu_{max}^{KBr}$ (cm$^{-1}$): 3600–2700, 1740, 1615, 1535, 1470, 1415, 1295, 1230, 1125, 1060, 730.

NMR (D$_2$O) δ: 0.74 (3H,t. J=7.0 Hz), 1.45 (2H, sex. J=7 Hz), 2.76 (3H,s), 4.12 (2H,q. J=7.0 Hz), 4.21 (1H,d. J=8.0 Hz), 5.01 (1H,d. J=8.0 Hz), 6.70–7.10 (3H,m).

Example 4

(a) N-methyl-L-threo-3-(3,4-dibenzyloxyphenyl) serine iso-propyl ester oxalate.

Melting point: 143°–145° C.

IR$\nu_{max}^{KBr}$ (cm$^{-1}$): 3280, 3000–2250, 1730, 1620, 1590, 1505, 1425, 1380, 1265, 1215, 1100, 1040, 810, 720.

NMR (CD$_3$OD) δ: 0.86 (3H,d. J=6.0 Hz), 1.14 (3H,d. J=6.0 Hz), 2.61 (3H,s), 4.08 (1H,d. J=7.5 Hz), 4.70–5.00 (2,m), 6.93 (2H,s), 7.10 (1H,s), 7.32 (10H,s).

(b) N-methyl-L-threo-3-(3,4-dihydroxyphenyl)serine iso-propyl ester oxalate.

This product showed the following IR data and NMR data.

IR$\nu_{max}^{KBr}$ (cm$^{-1}$): 3600–2300, 1725, 1605, 1460, 1400, 1280, 1220, 1100, 720.

NMR (D$_2$O) δ: 0.95 (3H,d. J=6.0 Hz), 11.7 (6H,d. J=6.0 Hz), 2.74 (3H,s), 4.19 (1H,d. J=7.5 Hz), 4.65–5.25 (3H,m). 6.89 (3H, br,s).

Example 5

(a) N-methyl-L-threo-3-(3,4-dibenzyloxyphenyl) serine n-butyl ester oxalate.

Melting point: 136°–138° C. (dec.).

IR$\nu_{max}^{KBr}$ (cm$^{-1}$): 3260, 2960, 2650, 2400, 1755, 1640, 1590, 1440, 1270, 1150, 1035, 825, 750.

NMR (CD$_3$OD) δ: 0.84 (3H,t. J=6.0 Hz), 0.95–1.50 (4H,m), 2.63 (3H,s), 3.95 (2H,t. J=6.0 Hz), 5.08 (1H,d. J=8.0 Hz), 5.08 (2H,s), 5.11 (2H,s), 6.94 (2H,s), 7.11 (1H,s), 7.15–7.50 (10H,m).

(b) N-methyl-L-threo-3-(3,4-dihydroxyphenyl)serine n-butyl ester oxalate (Compound D as identified hereinbefore).

This product showed the following IR data and NMR data.

IR$\nu_{max}^{KBr}$ (cm$^{-1}$): 3600–2400, 1735, 1610, 1530, 1290, 1225, 1160, 1020, 1060, 720.

NMR (CD$_3$OD) δ: 0.82 (3H,t. J=6.0 Hz), 0.90–1.60 (4H,m), 2.77 (3H,s), 3.80–4.35 (3H,m), 4.96 (1H,d. J=8.0 Hz), 6.75–7.00 (3H,m).

EXAMPLE 6

(a) D,L-threo-3-(3,4-dibenzyloxyphenyl)serine (1.50 g) and potassium carbonate (1.94 g) were suspended in 15 ml of acetone, and to the resulting suspension was added 1.94 g of dimethyl sulfate under stirring and ice-cooling. The whole mixture was stirred at room temperature for 15 hours, during which N-methyl-D,L-threo-3-(3,4-dibenzyloxyphenyl)serine methyl ester was formed. The reaction mixture was filtered to remove the insoluble matters, which were subsequently washed with 10 ml of acetone. The acetone washing was combined with the filtrate, to which was then added 15 ml of 1N hydrochloric acid. The whole mixture obtained was then allowed to stand at room temperature for 4 hours. The resultant reaction solution was washed twice with 10 ml of toluene and the remaining aqueous phase was concentrated by distilling off the acetone at a temperature of no more than 30° C. under reduced pressure. The residual concentrated solution was mixed with ethyl acetate so that two layers were formed. To this two layered mixture was added aqueous potassium carbonate solution under stirring, so that the mixture was made weakly alkaline. The ethyl acetate phase was separated, washed with saturated aqueous sodium chloride solution and then distilled under reduced pressure to remove the ethyl acetate therefrom. The residue obtained was purified by silica gel column chromatography (on Silica Gel 60 F 254, a product of Merck Co., U.S.A. as developed with chloroform-methanol (10:1)) to afford 1.15 g of N-methyl-D,L-threo-3-(3,4-dibenzyloxyphenyl)serine methyl ester as an oil. This oily product showed the following IR data and NMR data.

IR$\nu_{max}^{KBr}$ (cm$^{-1}$): 1750, 1600, 1510, 1430, 1380, 1280, 1140, 700.

NMR (CDCl$_3$) δ: 2.31 (3H,s), 2.78 (2H,br.), 3.12 (1H,d. J=7.5 Hz), 4.50 (1H,d. J=7.5 Hz), 5.13 (4H,s), 6.60–7.70 (13H,m).

(b) The methyl ester product as obtained in the above procedure (a) (0.5 g) was dissolved in 21.7 ml of methanol containing 0.2% (weight/volume) of hydrogen chloride, and to the resultant solution was added 0.1 g of 10% palladium-on-carbon as the hydrogenolysis catalyst. The catalytic reduction was effected for 3 hours under a current of hydrogen gas at 1 atm. to perform the removal of the hydroxyl-protecting benzyl groups. The reaction mixture was then filtered to remove the catalyst, and the filtrate was concentrated under reduced pressure. The residue was treated with isopropyl ether to give 0.22 g of N-methyl-D,L-threo-3-(3,4-dihydroxyphenyl)serine methyl ester hydrochloride in the form of a hygroscopic, faintly yellow colored crystalline powder. The crystalline product showed the following IR data and NMR data.

IR$\nu_{max}^{KBr}$ (cm$^{-1}$): 3200, 1750, 1610, 1530, 1450, 1290.

NMR (CD$_3$OD) δ: 2.63 (3H,s), 3.60 (3H,s), 4.11 (1H,d. J=6.0 Hz), 4.97 (1H,d. J=6.0 Hz), 6.50–7.00 (3H,m).

EXAMPLE 7

(a) N-methyl-L-threo-3-(3,4-dibenzyloxyphenyl) serine (1.00 g) was suspended in 30 ml of ethyl acetate, to which was then added a solution of diazomethane in ethyl ether. The mixture obtained was stirred at room temperature for 10 hours, during which N-methyl-L-threo-3-(3,4-dibenzyloxyphenyl)serine methyl ester was formed. The resulting reaction solution was mixed with 1 ml of methanol containing 10% (weight/volume) of hydrogen chloride. The whole mixture was distilled to remove the solvent therefrom, and the residue was recrystallized from acetone-ethyl ether to afford 1.03 g of N-methyl-L-threo-3-(3,4-dibenzyloxyphenyl)serine methyl ester hydrochloride as colorless, grain-like crystals. This crystalline product showed the following characteristics.

Melting point: 136°-138° C. (dec.).

IR$\nu_{max}^{KBr}$ (cm$^{-1}$): 3370, 2700, 1740, 1605, 1575, 1525, 1480, 1450.

NMR (CD$_3$OD) δ: 2.58 (3H,s), 3.54 (3H,s), 4.09 (1H,d. J=7.0 Hz), 4.96 (1H,d. J=7.0 Hz), 5.08 (2H,s), 6.84-7.53 (13H,m).

(b) The methyl ester product as obtained in the above procedure (a) (0.65 g) was dissolved in 10 ml of methanol, and to the resultant solution was added 0.07 g of 10% palladium-on-carbon as the hydrogenolysis catalyst. The catalytic reduction was effected for 3 hours under a current of hydrogen gas at 1 atm. to perform the removal of the hydroxyl-protecting benzyl groups. The reaction mixture was then filtered to remove the catalyst, and the filtrate was concentrated under reduced pressure. The residue was treated with isopropyl ether to give 0.35 g of N-methyl-L-threo-3-(3,4-dihydroxyphenyl)serine methyl ester hydrochloride in the form of a hygroscopic, faintly yellow colored crystalline powder. This crystalline product showed the following IR data and NMR data.

IR$\nu_{max}^{KBr}$ (cm$^{-1}$): 3600-2600, 1740, 1610, 1530, 1450, 1295, 1120, 1050, 1000, 820.

NMR (CD$_3$OD) δ: 2.63 (3H,s), 3.62 (3H,s), 4.13 (1H,d. J=6.5 Hz), 4.97 (1H,d. J=6.5 Hz), 6.75 (2H,s), 6.90 (1H,s).

EXAMPLE 8

(a) N-methyl-L-threo-3-(3,4-dibenzyloxyphenyl) serine (1.0 g) was suspended in 20 ml of methanol, and to the resulting suspension was added thionyl chloride (1.0 ml) under stirring and ice-cooling. The mixture obtained was stirred at room temperature for 30 minutes and then at 45°-50° C. for 5 hours.

The reaction solution obtained was allowed to stand overnight and then was distilled under reduced pressure to remove the solvent, and the residue was taken up in a volume of ethyl acetate. The resultant solution was washed with aqueous 5% sodium hydroxide solution and then with water, followed by drying the organic phase over anhydrous sodium sulfate. After removing the drying agent by filtration, the dried solution was distilled under reduced pressure to remove the solvent therefrom, and the residue was dissolved into 3 ml of methanol, and to the methanolic solution were added 0.12 g of L-tartaric acid and then 10 ml of ethyl ether. The whole mixture was allowed to stand in an ice chamber until the crystals deposited. The crystalline product obtained was removed by filtration, washed with ethyl ether and dried to afford 0.36 g of N-methyl-L-threo-3-(3,4-dibenzyloxyphenyl)serine methyl ester L-tartarate as colorless needles having a melting point of 131°-133° C.

This product showed the following IR data and NMR data.

IR$\nu_{max}^{KBr}$ (cm$^{-1}$): 3300, 3100-2300, 1740, 1590, 1510, 1430, 1390, 1300, 1265, 1220, 1135, 1070 1000, 740, 700.

NMR (CD$_3$OD) δ: 1.58 (3H,s), 3.46 (3H,s) 4.00 (1H,d. J=8.0 Hz), 4.39 (2H,s), 5.04 (2H,s), 5.06 (2H,s), 6.86 (2H,s), 7.06 (1H,s), 7.25 (10H,br.s).

(b) The N-methyl-L-threo-3-(3,4-dibenzyloxyphenyl) serine methyl ester L-tartarate obtained as above (0.35 g) was dissolved in 20 g of methanol, and to the resulting solution was added 0.07 g of 10% palladium-carbon catalyst. The hydrogenolysis was carried out at room temperature for hours under a current of hydrogen gas at 1 atm. to effect the removal of the hydroxyl-protecting benzyl group. The reaction mixture was then filtered to remove the catalyst, and the filtrate was concentrated in vacuo. The residue was treated with ethyl ether to crystallize the deprotected product. The crystalline product as formed was recovered by filtration, washed with ethyl ether and dried to yield 0.21 g of N-methyl-L-threo-3-(3,4-dihydroxyphenyl)serine methyl ester L-tartarate.

This L-tartarate product showed the following IR data and NMR data.

IR$\nu_{max}^{KBr}$ (cm$^{-1}$): 3600-2500, 1735, 1600, 1530, 1440, 1400, 1300, 1265, 1220, 1135, 1070, 790, 675.

NMR (D$_2$O) δ: 2.67 (3H,s), 3.68 (3H,s), 4.25 (1H,d.J=6.0 Hz), 4.46 (2H,s), 5.06 (1H,d.J=6.0 Hz), 6.86 (3H,br.s).

EXAMPLE 9

The procedures of Example 8 were repeated using p-toluenesulfonic acid in place of the L-tartaric acid. Thus, the reactions and the treatments were carried out in the same manner as in Example 8, except that the L-tartaric acid was replaced by p-toluenesulfonic acid. The under-mentioned compounds were obtained.

(a) N-methyl-L-threo-3-(3,4-dibenzyloxyphenyl) serine methyl ester p-toluenesulfonate.

Melting point: 161°-163° C.

IR$\nu_{max}^{KBr}$ (cm$^{-1}$): 3125, 2875, 2650, 1745, 1605, 1515, 1470, 1425, 1320, 1285, 1225, 1140, 1035, 1010, 915, 815, 750, 700.

NMR (CD$_3$OD) δ: 2.30 (3H,s), 2.55 (3H,s), 4.08 (1H,d. J=7.0 Hz), 4.96 (1H,d.J=7.0 Hz), 5.06 (4H,s), 6.89 (2H,s), 7.00-7.50 (12H,m), 7.64 (2H,d. J=7.0 Hz).

(b) N-methyl-L-threo-3-(3,4-dihydroxyphenyl)serine methyl ester p-toluenesulfonate IR$\nu_{max}^{KBr}$ (cm$^{-1}$): 3600-2600, 1740, 1605, 1450, 1290, 1170, 1225, 1140, 1015, 820, 785.

NMR (CD$_3$OD) δ: 2.30 (3H,s), 2.56 (3H,s), 3.59 (3H,s), 4.03 (1H,d. J=7.0 Hz), 4.91 (1H,d.J=7.0 Hz), 6.67 (2H,s), 6.81 (1H,s), 7.11 (2H,d. J=7.0 Hz), 7.62 (2H,d.J=7.0 Hz).

What we claim is:

1. An N-methyl-L-threo-3-(3,4-dihydroxyphenyl)serine methyl ester or ethyl ester or a pharmaceutically acceptable acid addition salt thereof.

2. N-methyl-L-threo-3-(3,4-dihydroxyphenyl)serine methyl ester.

3. N-methyl-L-threo-3-(3,4-dihydroxyphenyl)serine ethyl ester.

4. An α-adrenergic and β-adrenergic agent comprising an N-methyl-L-threo-3-(3,4-dihydroxyphenyl)serine (C$_1$-C$_2$) alkyl ester or a pharmaceutically acceptable acid addition salt thereof as the active ingredient in an amount effective to stimulate both the α-adrenergic and β-adrenergic functions of the central nervous system of mammalian animals, in association with a pharmaceutically acceptable carrier for the active ingredient.

5. A method of stimulating both the α-adrenergic and β-adrenergic functions of the central nervous system of a mammalian animal, which comprises administering orally, intravenously, intraperitoneally or rectally to said animal an effective amount of N-methyl-L-threo-3-(3,4-dihydroxyphenyl) serine methyl ester or ethyl ester or a pharmaceutically acceptable acid addition salt thereof.

* * * * *